United States Patent
Aldcroft et al.

(10) Patent No.: US 6,905,698 B1
(45) Date of Patent: Jun. 14, 2005

(54) PARTICULATE CARRIER FOR BIOCIDE FORMULATIONS

(75) Inventors: Derek Aldcroft, Cheshire (GB); Helen Jones, Cheshire (GB); Dafydd Turner, Powys (GB); Michel Edge, Manchester (GB); Julie Robinson, Lancashire (GB); Kenneth Seal, Cheshire (GB)

(73) Assignee: Ineos Silicas Limited, Warrington (GB)

( * ) Notice: Subject to any disclaimer, the term of this patent is extended or adjusted under 35 U.S.C. 154(b) by 0 days.

(21) Appl. No.: 09/763,916

(22) PCT Filed: Aug. 24, 1999

(86) PCT No.: PCT/GB99/02796

§ 371 (c)(1),
(2), (4) Date: May 11, 2001

(87) PCT Pub. No.: WO00/11949

PCT Pub. Date: Mar. 9, 2000

(30) Foreign Application Priority Data

Aug. 28, 1998 (GB) .............................. 9818778

(51) Int. Cl.⁷ ............................... A01N 25/26
(52) U.S. Cl. ................. 424/405; 424/406; 424/407; 424/409; 424/421; 424/682; 424/724; 514/372
(58) Field of Search ............... 424/405, 407, 424/421, 724, 682, 409; 514/372

(56) References Cited

U.S. PATENT DOCUMENTS

| | | | |
|---|---|---|---|
| 4,552,591 A | 11/1985 | Millar | |
| 4,579,779 A | 4/1986 | Ohno | |
| 5,229,124 A | 7/1993 | Rei et al. | |
| 5,693,444 A | * 12/1997 | Takagi et al. | ............ 430/110.4 |
| 5,730,996 A | * 3/1998 | Beall et al. | ................. 424/405 |

FOREIGN PATENT DOCUMENTS

| | | |
|---|---|---|
| EP | 0112610 A1 | 7/1984 |
| EP | 0353075 A2 | 1/1990 |
| EP | 0457435 A2 | 11/1991 |
| EP | 0832561 A2 | 4/1998 |
| EP | 0922386 A2 | 6/1999 |
| JP | 0466505 | 3/1992 |
| JP | 10 237716 | 9/1998 |
| WO | 93/09817 | 5/1993 |
| WO | 94/11302 | 5/1994 |
| WO | 95/31508 | 11/1995 |

* cited by examiner

Primary Examiner—Neil S. Levy
(74) Attorney, Agent, or Firm—Mayer Brown Rowe & Maw LLP

(57) ABSTRACT

A particulate carrier material is impregnated with a biocidal formulation and serves as a vehicle for introduction of the biocide into a liquid-based media, such as a surface coating or surface cleaning compositions, in order to allow controlled release of the biocide to combat bacterial, fungal, algal or like growth for an extend period of time.

38 Claims, No Drawings

PARTICULATE CARRIER FOR BIOCIDE FORMULATIONS

CROSS REFERENCE TO RELATED APPLICATION

This application is the National Phase application of International Application No. PCT/GB99/002796, filed Aug. 24, 1999, which designates the United States and was published in English. This application in its entirety, is incorporated herein by reference.

This invention relates to an inorganic particulate carrier particle for use as a vehicle for introducing biocides into liquid-based media such as paints, lacquers, plastisols, oil drilling fluids and surface cleaning compositions. The term "biocide" as used herein is to be understood to refer to agents such as germicides, bactericides, fungicides, algicides and the like, which are used for their ability to inhibit growth of and/or destroy biological and/or microbiological species such as bacteria, fungi, algae and the like.

Biocidal agents (biocides) capable of protecting paint, lacquer, plastisol, oil drilling fluids and surface cleaning compositions are well known in the art. U.S. Pat. Nos. 4,129,448 and 4,165,318 are illustrative of prior art which discloses the use of biocides to stabilise mildew growth in acrylic emulsion polymer paints. U.S. Pat. No. 3,699,231 discloses the use of an aldehyde/carbamate mixture to inhibit bacterial growth. Other inhibiting admixtures are known containing isothiazolones and chlorinated derivatives of which U.S. Pat. No. 3,929,561 and U.S. Pat. No. 4,295,932 are examples. All the above disclosures describe a method for protecting the bulk formulation by adding the biocide directly to the composition.

Attempts to control the release of biocide to inhibit bacterial and fungal growth have centred around the use of sol gel chemistry to entrap the biocide but allow release thereof by diffusion from the hydrogel network. This approach is exemplified by EP-A-0602810, EP-A-0736249, GB-A-2235462 and GB-A-1590573 and U.S. Pat. No. 5,229,124. Applications of sol gel entrapment technology for the controlled release of biocide have however been limited owing to the need for the components, that form the encapsulation system "in situ", to be included in a particular formulation and be compatible with the remainder of the ingredients.

Another approach which involves the encapsulation of organic liquids such as perfumes, food flavours, pesticides and fungicides is disclosed in U.S. Pat. No. 4,579,779. Here the organic liquid is combined with particles of amorphous silica having a pore size distribution wherein 50% of the integrated micropore volume is constituted by micropores having a radius up to 500 Angstrom Units (AU), the liquid and particles being combined in such a way that droplets of the organic liquid are encompassed within a shell of silica particles. The silicas employed are Tokusil PR and Tokusil NR, made by Tokuyama Soda Co. Ltd. The average particle size and BET surface area for Tokusil PR and Tokusil NR are 100 and 130 microns and 198 and 195 $m^2/g$ respectively.

The impregnation of mineral particles with biocides is also known. U.S. Pat. No. 4,552,591 describes a composition intended to protect polymer dispersions used in oil field water treatment. This composition comprises a liquid biocide adsorbed on mineral adsorbents, granular or bead-like in nature, such as diatomaceous earth, silica, metal oxides (alumina bauxite, magnesia iron oxide), clays, zeolites, resins and waxes. Apart from a general reference to "well known adsorbents having a high degree of surface area", no mention is made of key properties such as surface area, pore volume, pore size, pore size distribution. The preferred adsorbent is diatomaceous earth and whilst this material has a high propensity for liquids, there is no evidence that the carrier particle will retain biocide within its pore system and provide controlled release to an aqueous based composition.

The present invention seeks to provide an improved biocide-carrying carrier particle.

According to one aspect of the present invention there is provided a particulate composition of matter comprising porous inorganic carrier particles having biocide adsorbed within the pore system thereof and having a retention factor (as defined herein) of at least 0.6, preferably at least 0.8.

The retention factor, R, referred to above is determined from the equation $R=A/P$, where A represents the percentage active ingredient by weight remaining in the pore system after contacting with water according to the conditions defined herein and P represents the potency (Minimum Inhibition Concentration in mg of active ingredient per liter) of the biocide determined with respect to the reference microorganism *Aureobasidium pullulans* using the procedure defined herein.

The usefulness of the inorganic carrier particle will depend on the particular biocide being used, its effectiveness at various activity levels and the quantity of biocide (active ingredient) adsorbed and retained in the pore system. The amount of biocide deemed to be effective in the pore system will depend on the potency of the biocide, that is, the minimum concentration of active ingredient to prevent microbial or fungal growth. For the purposes of the present invention, the reference microorganism is *Aureobasidium pullulans*. Commonly used biocides are 2-Octyl-4-isothiazolin-3-one (OIT) and a blend of 2-Methyl-4-isothiazolin-3-one (MIT) and 5-Chloro-2-Methyl-4-isothiazolin-3-one (CIT), known as (CIT/MIT). For these biocides, the Minimum Inhibition Concentration (MIC) is 36 and 5 mg of active ingredient per liter for OIT and CIT/MIT respectively.

Prior to contact with liquid media into which the particles are to be introduced, the particles preferably carry at least 30% by weight of biocide in aqueous solution or water/organic solution.

Such particles will usually be chemically inert with respect to the liquid media into which they are introduced.

A feature of the invention is the ability of the particles, when formulated into solvent or aqueous based compositions, to retain the biocide within the pore system thereof to such an extent that release of the biocide into the liquid media is sufficiently retarded in order to provide an extended period of biocidal, e.g. bactericidal and/or fungicidal, activity.

Preferably the inorganic particles have an activated micropore system. Under the IUPC system, a micropore is one having a diameter of no more than 30 AU, activation usually being achieved by thermal treatment. Whilst not wishing to be bound by theory it is thought that the carriers that contain an activated micropore system are capable of adsorbing the biocide molecules in preference to water and other substrate molecules. The invention therefore encompasses a particulate composition of matter comprising porous inorganic carrier particles having biocide adsorbed within the pore system thereof, the carrier particles having an activated micropore system.

In order to secure appropriate retention of biocide, a preferred inorganic carrier particle has a pore area of at least 25 $m^2/g$, preferably at least 30 $m^2/g$, more preferably at least 40 $m^2/g$, and up to about 300 $m^2/g$, e.g. 50 $m^2/g$ to 250 $m^2/g$, in the pore size range of from about 20 to about 50 Angstroms, and a BET surface area of at least 200 $m^2/g$ and more preferably at least 300 $m^2/g$, typically 350 $m^2/g$ to 1200 $m^2/g$. The invention therefore also encompasses a particulate composition of matter comprising porous inorganic carrier particles having biocide adsorbed within the pore systems thereof, the carrier particles having a pore area of at least 25 $m^2/g$ in the pore size range of from about 20 to about 50 Angstroms, preferably with a BET surface area of at least 200 $m^2/g$.

The weight mean particle size of the inorganic carrier particles employed in the various aspects of the present invention id less than 50 microns, more usually less than 40 microns, and typically within the range of 1 to 30 microns.

The porous inorganic carrier particles preferably have a biocide adsorption capacity of at least 10%, more preferably at least 15% and most preferably at least 20% by weight of the carrier particle plus biocide. The adsorption capacity in this instance is the amount of biocide which is retained in the pore system of the porous inorganic carrier particle when the particle containing the biocide is contacted with water as defined herein. The desired biocide adsorption capacity of the carrier particle will, in practice, depend on the particular biocide employed and its potency.

The biocide generally comprises a composition to control and prevent the germination and growth of bacteria, fungi and algae and include the following suitable chemical types: aldehydes, formaldehyde condensates, triazines, phenolics, carbonic acid esters, amides, e.g., N-(3,4-dichlorphenyl)-N, N-dimethyl urea, carbamates, e.g., methyl-N-benzimidazol-2-methylcarbamate, thiocarbamates thiocyanates, dibenzamidines, pyridine derivatives, triazoles, thiazoles, isothiazolones,eg, 2-methyl-4-isothiazolin-3-one, N-haloalkylthio compounds, e.g. N-dichlorofluoromethylthiophthalimide and the like. The isothiazolin-3-ones are the presently preferred biocides.

Suitable isothiazolin-3-ones include 2-methyl-4-isothiazolin-3-one, 2-ethyl 4-isothiazolin-3-one, 2-propyl-4-isothiazolin-3-on, 2-butyl-4-isothiazolin-3-one, 2-amyl-4-isothiazolin-3-one, 5-chloro-2-methyl-4-isothiazolin-3-one, 5-bromo-2-methyl-4-isothiazolin-3-one, 5-iodo-2-methyl-4-isothiazolin-3-one, 5-chloro-2-butyl-4-isothiazolin-3-one, 5-bromo-2-ethyl-isothiazoline-3-one, 5-iodo-2-amyl-4-isothiazolin-3-one, 1,2-benzisothiazolin-3-one, 2-n-octyl-4-isothiazolin-3-one, 4,5-dichloro-2-n-octyl-4-isothiazolin-3-one and other similar analogues and homologues within the genus.

Advantageously the biocide is selected from a mixture of 5-chloro-2-methyl-4-isothiazolin-3-one and 2-methyl-4-isothiazoline-3-one, typically in the weight ratio of between 1.5 and 2.5:1, e.g. in the range 2.7 to 3:1; 2-n-octyl-4-isothiazolin-3-one; or 4,5-dichloro-2-(n-octyl)-4-isothiazolin-3-one.

The carrier particles suitable may be constituted by amorphous silicas, amorphous aluminas, pseudoboehmites (a form of microcrystalline aluminium hydroxide), Y-zeolites or dealuminated Y-zeolites. In the case of the latter, the Si:Al ratio should be in the range preferably from about 5:1 to about 33:1.

Adsorption of the biocide is usually achieved by mixing the carrier particles with the biocide and such mixing may be carried out in a variety of ways known to those skilled in the art. For example, the biocide solution may be sprayed onto the porous inorganic particles in a rotary drum, or while they are being conveyed on a conveyor belt. Non-limiting examples of powder mixers include, Nauter conical mixers, double cone mixers, trough mixers, fluid bed mixers and various rotating blade vessel mixers. In all these mixers the powder charge is fluidised by a paddle, screw, air agitation or by mechanical rotation. The biocide solution is sprayed onto the particles and mixing continued until the take-up of biocide solution to the desired level is obtained (usually so that the porous inorganic particles maintain a free flowing consistency). The biocide/inorganic particle composition can then be dropped by gravity into suitable containers.

The amount of biocide added to the porous inorganic carrier particles will depend on the particular biocide being used and its effectiveness at various activity levels. Thus the concentrated biocide is usually diluted to afford an activity level commensurate with microbial inhibition. Further, a solution 10% by weight biocide in an appropriate solvent (10% active) has biocidal properties that will vary depending on the particular biocide and the amount of the solution which is added to a particular microbial culture. Accordingly, a biocide may be added to the porous inorganic particles undiluted (100% active) or it may be diluted with a solvent to a lower activity (as low as 10% active). This is particularly the case for the isothiazolin-3-ones where the pure biocide is usually diluted with water or water alcohol blends to achieve levels of from about 1 to about 60%, preferably from about 2 to about 50%, e.g. about 5 to about 25%, active by weight.

The biocide-impregnated carrier particles are particularly useful in surface coating compositions, e.g. paints, lacquers, and plastisols.

According to a second aspect of the invention there is provided a surface coating composition incorporating a biocide-carrying particles in accordance with said first aspect of the invention.

Typically the composition comprises a film forming material, which is usually polymeric in nature, a solvent and various additives, such as pigments, dyes, dispersing agents, surfactants and antifoaming agents. The total non-volatile content of the composition, usually referred to as the solids content, can vary widely. Often it is desirable that the non-volatile content should be at least 30% by weight of the formulation in order that a practical amount of film forming material is present in the dried/cured film. The compositions often can be satisfactorily formulated at a non-volatile content as low as 10% by weight or as great as 100% by weight but, in the latter case, thinning may be necessary at this concentration to provide satisfactory application. The preferred non-volatile concentration is from about 30 to about 65% by weight, irrespective of whether the solvent is organic-based or water.

Where the composition is water based, it generally comprises an aqueous dispersion of the polymer in an emulsion form as the major film forming component whereas a solvent borne composition usually employs the polymer per se, e.g. in solution. Examples of such polymers include homopolymers and copolymers of: (1) vinyl esters of an aliphatic acid having 1 to 18 carbon atoms, especially vinyl acetate; (2) acrylic acid esters and methacrylic acid esters of an alcohol having 1 to 18 carbon atoms, especially methyl acrylate, ethyl acrylate, butyl acrylate, 2-ethylhexyl acrylate, methyl methacrylate, ethyl methacrylate and butyl methacrylate; and (3) mono and di-ethylenically unsaturated hydrocarbons, such as ethylene iso-butylene, styrene and aliphatic dunes, such as butadiene, isoprene and chloroprene.

Poly(vinyl acetate) and copolymers of vinyl acetate with one or more of the following compositions: vinyl versatate or vinyl esters of fatty acids having 3 to 18 carbon atoms, vinyl chloride, vinylidene chloride, styrene, vinyl toluene, acrylonitrile, methacrylonitrile, mono or di-fumaric or -maleic acid esters, such as of the alkanols having 1 to 4 carbon atoms, including for example, monomethyl fumerate, diethyl maleate or fumerate, dibutyl maleate or monobutyl maleate, or one or two of the acrylic and methacrylic esters mentioned above may be used as the film forming components where the paint is aqueous based. Similarly, copolymers of one or more of the acrylic or methacrylic acid esters mentioned above with one or more of the following monomers: vinyl acetate, vinyl esters of higher fatty acids, the mono or di-alkyl esters of itaconic acids, the mono or di-alkyl esters of fumaric acid or the mono or di-alkyl esters of maleic acid, such as esters of methanol ethanol, or butanol, vinyl chloride, vinylidene chloride, styrene, vinyltoluene, acrylonitrile and methacrylic nitrite, may be used in the composition according to said second aspect of the invention.

The surface coating composition can contain additional materials to vary the properties and to adapt the composition for different uses. For example plasticisers can be added together with a range of pigments and dyes. The relative proportions of vehicle to pigment may fall in a wide range, such as from a ratio of 1:20 to 20:1 but for most formulations the range is 1:5 to 5:1. Cellulose derivatives such as methylcellulose, carboxylmethyl cellulose or hydroxyethyl cellulose can be used as bodying agents. Antifoam agents can be included to control foam generation caused by the presence of surfactants to assist the dispersion of pigments and dyes. Other auxiliary materials that may be used include dispersing agents, such as, aromatic sulphonates condensed with formaldehyde, humectants such as water soluble gums, glycol laurate, propylene glycol, diethylene glycol and the like, thickeners/body agents, perfume and like materials including neutralising and masking agents which are used to overcome odours or impart pleasant odours; other resinous materials such as drying oils or latices of styrene or of styrene and butadiene.

The amount of porous inorganic carrier containing the biocide incorporated in a surface coating composition will vary according to factors, such as, the composition itself, particular inhibitor composition, the conditions of use of solvent, water or polymer dispersion and the extent of prior contamination with micro-organisms, the time period of growth inhibition desired, the requirements of the Health and Safety exposure limits. Usually, to afford adequate protection for many applications, the amount of biocide-containing carrier particle added to the surface coating composition will be such that the active biocide constitutes from about 0.01% to about 3%, e.g. 0.01% to 2%, by weight of the composition.

The porous inorganic carrier containing the biocide may be incorporated into the surface coating composition by adding the particulate carrier (i) to water used in the formulation, (ii) to the polymer dispersion or (iii) to the total formulation. This is optimally carried out in a containing vessel which can be readily agitated with a high speed disperser such as a Silverson mixer.

The biocide-containing particles of the invention also have application in surface cleaning compositions in order to enhance the performance of such compositions. Accordingly, in a third aspect of the present invention there is provided a surface cleaning composition incorporating biocide-carrying particles according to said one aspect of the invention.

The surface cleaning composition preferably comprises an aqueous dispersion of a surfactant and an inorganic builder, such as, an aluminium silicate or zeolite and, optionally, other components such as one or more of the following: water soluble complex formers or precipitating agents for calcium ions; abrasives; water soluble or water dispersible organic solvents; hydrotropes; and soil suspending agents.

Suitable surfactants of the sulphonate type used in these formulations can include alkyl benzene sulphonates, in which the alkyl group has from 9 to 15 carbon atoms, alkane sulphonates, esters of alpha-sulpho fatty acids, sulphuric acid mono esters of primary aliphatic $C_{10}$ to $C_{12}$ alcohols, sulphated fatty acid alkanol amides, fatty acid monoglycerides with $C_{10}$ to $C_{20}$ fatty acids and sulphates of primary or secondary aliphatic $C_{10}$ to $C_{20}$ alcohols that have been reacted with 1 to 6 moles of ethylene oxide. Surfactants having anionic groups may be present in the form of their sodium, potassium, and ammonium salts or in the form of water soluble salts of organic bases, such as mono-, di or tri ethanol-amine.

Suitable non-ionic surfactants are addition products of ethylene oxide and an alphatic $C_{10}$ to $C_{20}$ alcohol or an alkyl phenol, fatty amine or fatty acid, ethoxylated products of aliphatic alcohols, $C_{10}$ to $C_{20}$ oxoalcohols and secondary aliphatic alcohols having 12 to 18 carbon atoms. Suitable non-ionic surfactants also include surface active amine oxides such as N-dodecyl-N,N-dimethyl amine oxide, N-tetradecyl-N,N-dihydroxy ethyl amine oxide, N-hexadecyl-N, N-bis(2,3-dihydroxy-propyl)amine oxide.

In addition to a hydrophobic, generally through an aliphatic group, suitable zwitterionic surfactants which contain both hydrophilic acidic groups and basic groups are useful. Zwitterionic compounds having four-fold substitution, the substituents belonging to the betaine group, (i.e. quaternary ammonium group) can also be formulated into the composition. Particularly useful are the carboxy, sulphonate and sulphate betaines of nitrogen. Typically representative examples of zwitterionic surfactants are compounds of 3-(N-hexadecyl-N,N-dimethylammonium)-propane sulphonate, 3-(N-coconut-alkyl-N, N-bis-(2,3-dihydroxy propyl) ammonium)-propyl sulphonate.

Suitable complex formers or precipitating agents for calcium ions or heavy metal ions include inorganic agents, such as pyrophosphate, tripolyphosphate, higher polyphosphates and metaphosphates. Also organic agents, such as salts of aminopoly-carboxylic acids, for example, nitrile triacetic acid, ethylene-diamine-tetra-acetic acid, of citric acid, gluconic acid; of carboxy-methyl-ether-carboxylic acids, having molecular weights in excess of 350, for example, polyacrylic acid, poly-alpha-hydroxyacrylic acid can be used. Also useful are the water soluble salts of the phosphono-alkane-polycarboxylic acids and the amino- and hydroxy-substituted alkane polyphosphonic adds.

Soil suspending agents that may be employed are generally water soluble colloids, such as water soluble salts of polymeric carboxylic acids, glue, gelatine, salts of ether-carboxylic acids or ether sulphonic acids of starch and cellulose, or salts of acidic sulphuric acid esters of cellulose or starch. Polyamides containing water soluble acidic groups are also suitable for this purpose. In addition, soluble starch preparations and starch products, such as decomposed starche aldehyde starches and polyvinylpyrrolidone may also be used.

The most suitable organic solvents that may be employed are alcohols and ether alcohols which are water-soluble or can be emulsified with water, for example ethanol, isopropyl alcohol, butanol, amyl alcohol, ethylene glycol, diethylene glycol.

The amount of porous inorganic carrier containing the biocide incorporated in the surface cleaning composition will vary according to factors such as those mentioned previously in connection with surface coating compositions. Typically, a surface cleaning composition according to said third aspect of the invention will incorporate an amount of biocide-carrying particles such that the biocide constitutes about 0.1 to about 3% by weight of the cleaning composition.

The biocide-containing particles may be incorporated into the surface cleaning composition by adding the particulate carrier (i) to the water used in the formulation, (ii) to the additive dispersion, or (iii) to the total formulation. The addition of the inorganic carrier particulate containing the biocide is optimally carried out in a containing vessel which can be readily agitated with a rotating blade, propeller or turbine.

The biocide-impregnated particles are particularly useful in sealant compositions. Accordingly, in a fourth aspect of the present invention there is provided a sealant composition incorporating biocide carrying particles according to said one aspect of the invention.

A sealant is a material that is typically installed in a gap or joint to prevent water, wind, dirt or other contaminants from passing through the joint or gap. This joint or gap may be a fixed point, but is often an expansion joint also known as a working joint. Typically, a sealant composition comprises a blend of a polymer and/or copolymer, moisture scavengers, and cross-linkers as well as conventional additives including fillers, pigments or colorants, rheology modifiers adhesion/promoters, solvents and curing catalysts. The polymers commercially utilised can be classified as silicones, urethanes, polymeric-sulphides, acrylics and butyl polymers. Curing mechanisms involved with the majority of sealing compositions include moisture reactive, moisture releasing (latex) and addition reactive chemistry.

The amount of porous inorganic carrier containing the biocide that can be incorporated in a sealant composition will vary according to many factors, such as the composition itself, the particular inhibitor composition used, the conditions of use of the solvent, water or polymer dispersions (aqueous or non-aqueous), the extent of prior contamination with microorganisms, the time period of growth inhibition desired and the requirements of the Health and Safety Exposure Limits. Usually, to afford adequate protection for many applications, the amount of biocide-containing carrier particle added to the sealant composition will be such that the active biocide constitutes from about 0.01 to about 3%, e.g. 0.01 to 2%, by weight of the composition.

The porous inorganic carrier containing the biocide may be incorporated into the sealant composition by adding the particulate carrier to the blend of ingredients. This is optimally carried out in a containing vessel, which can be agitated with a high shear mixer such as the Werner Pfleiderer compounder or sigma-blade batch mixers.

The biocide-containing particles of the invention also have an application use in tiling or grouting compositions in order to enhance the performance of such compositions. Accordingly, in a fifth aspect of the present invention there is provided a tiling or grouting composition incorporating biocide-carrying particles according to said one aspect of the invention.

The tiling/grouting composition can be gypsum or cement based and contain other admixture additives, such as, for example, sand, perlite and vermiculite and can contain aeration agents and plasticisers to improve performance. The cements normally utilised in these compositions are based on Portland cement or alumina cement.

The amount of porous inorganic carrier containing the biocide incorporated into the tiling/grouting composition will vary according to factors such as the composition itself, particular inhibitor composition, the conditions of use of solvent or admixture dispersions (usually aqueous) and the extent of prior contamination with microorganisms, the time period of growth inhibition desired and the requirements of the Health and Safety Exposure Limits. Usually to afford adequate protection for many applications, the amount of biocide containing carrier particle added to the tiling/grouting composition will be such that the active biocide constitutes from about 0.01 to 3% e.g. 0.01% to 2%, by weight of the composition.

The porous inorganic carrier containing the biocide may be incorporated into the tiling or grouting composition by adding the particulate carrier to the blend of ingredients. This is optimally carried out in a containing vessel that is agitated with a low to medium shear mixer such as a Ross mixer and other planetary types common in industry.

The biocide containing particles of the invention also have an application in drilling mud in order to enhance the performances of such compositions. Accordingly, in a sixth aspect of the present invention there is provided a drilling mud composition incorporating biocide carrying particles according to said one aspect of the invention.

The drilling mud composition comprises polymers used in oilfield fluids including, for example, starches, carboxymethylcellulose polymers, guar gums, polysaccharides and polyacrylamides to enhance its performance.

The amount of porous inorganic carrier containing the biocide incorporated in a drilling mud composition is dependent upon the following: the conditions of use of the solvent; the water or polymer dispersion (aqueous or non-aqueous) and the extent of prior contamination with microorganisms; the time period of growth inhibition desired and the requirements of the Health and Safety Exposure Limits. Usually to afford adequate protection for many applications, the amount of biocide containing carrier particle added to the drilling mud composition will be such that the active biocide constitutes from about 0.1 to about 3%, e.g. 0.01% to 2%, by weight of the composition. The biocide containing particles of the invention may be incorporated into the oilfield water or oilfield fluid polymer by adding the composition into: (i) water used for making the polymer solution, (ii) concentrated polymer solution and/or (iii) dilute polymer solution using a batch dosing procedure. The protected oil drilling mud formulations can be prepared by mixing the biocide carrying particles with the prepared solution in a containing vehicle agitated with a conventional stirring device.

Definitions and Procedures

The porous inorganic particulate carrier biocide compositions of the invention are defined in terms of the properties and texture of the porous inorganic particulate together with their capability to adsorb biocide and retain it within the specifically selected pore size range.

i) Weight Mean Particle Size

The weight mean particle size of the porous inorganic carrier particulate is determined using a Malvern Mastersizer model X, with a 45 mm lens and MS15 sample presentation unit. This instrument made by Malvern Instruments, Malvern, Worcestershire, UK uses the principle of Mie scattering, utilising a low power Helium/Neon laser. Before measurement the sample is dispersed ultrasonically in water for 5 minutes to form an aqueous suspension. This suspension is stirred before it is subjected to the measurement procedure outlined in the instruction manual for the instrument. The measurement is carried out utilising a 45 mm lens in the detector system.

The Malvern Mastersizer measures the weight particle size distribution of the silica or reference material. The weight mean particle size ($d_{50}$) or 50 percentile, the 10 percentile ($d_{10}$) and the 90 percentile ($d_{90}$) are readily obtained from the data generated by the instrument.

ii) BET Surface Area

Surface area is determined using standard nitrogen adsorption methods of Brunauer, Emmett and Teller (BET), using a single point method with a Sorpty 1750 apparatus supplied by Carlo Erba company of Italy. The sample was outgassed under vacuum at 270° C. for 1 hour before measurement.

iii) High Performance Liquid Chromatography (HPLC)

High Performance Liquid Chromatography(HPLC) was used to evaluate the concentration of biocide in a solvent system. Typically the sample of biocide in a liquid sample is loaded onto a Nucleosil $10C_{18}$ column and eluted along the column at a fixed flow rate by the use of eluting solvents and a pump. As with other chromatographic methods the materials loaded onto the column will pass through the column packing at different rates. The time at which a material exits the column is known as the retention time and is characteristic of the compound being analysed and the method being used. As the components of the mixture exit the column they are analysed by an accurate internal or external UV/Visible spectrophotometer.

The use of HPLC involves three separate steps. Firstly the mobile phase/diluent has to be selected and then prepared. Choosing the most appropriate solvents is often a matter of trial and error. For OIT, methanol, water and acetic acid in a 65:35:0.2 ratio has been found to be the most suitable, whilst for CIT/MIT, methanol, water and acetic acid in a 65:35:0.4 ratio gives the best result. Preparation of the mobile phase involves adding the relevant quantities of solvent, ensuring complete mixing and then degassing using an ultrasonically agitated bath. The second step is calibration of the HPLC equipment which is achieved by analysing a sample of known composition and concentration. The analytical standard should be prepared using the same mobile phase/diluent as that to be used in the determination. The final step is to produce calibration graphs for the biocides used in the study. This is achieved by preparing samples of known quantities of biocide and obtaining concentration values from the generated chromatograms. These concentration values are then used to plot a calibration graph for each biocide used in the study. Test samples can then be run on the HPLC and the quantity of biocide present in the test solutions derived. This method was used to validate the UV/VIS spectroscopic method referred to below.

iv) UV/VIS Spectroscopy

Second derivative UV-Visible spectroscopy has been employed as an alternative to HPLC for determining the biocide concentration in either water or propylene glycol/water. The advantages of this technique are its simplicity of use and high degree of accuracy. Also single- and multi-component systems can be analysed. The deflections in a second derivative spectrum are not proportional to the absorption values in the original spectrum. Rather they are proportional to the slope of the latter providing it was scanned in absorption mode. Positive and negative slopes are shown as positive and negative deflections in the derivatised spectrum. It is the position of the absorption and the relation of the extremes that are of interest in this method. Its application here was as a means of monitoring the amount of biocide leached into a solvent and as such the procedure used to evaluate the results was to measure the amplitude of deflection (delta A) on a peak to peak basis. In this method, the absolute distance between a maximum and an adjoining minimum is determined as a characteristic of the species under investigation. This distance is then compared with a standard calibration to attain the concentration of the sample. A Perkin-Elmer lamda 7 spectrophotometer was used in conjunction with the lamda 16 WINDOWS software package to determine accurate values of (delta A) from the derivative spectra obtained. The software package can be obtained from Perkin Elmer of Post Office Lane, Beaconsfield, Bucks HP9 1QA, United Kingdom.

v) Pore Area in a Pore Size Range

The nitrogen adsorption isotherm is determined using a multi-point method with ASAP 2400 apparatus supplied by Micrometrics of the USA. The samples are outgassed under vacuum at 270° C. for at least one hour before measurement. This apparatus also enables the pore size distribution from the adsorption branch of the isotherm to be calculated. This can be expressed in terms of the cumulative pore area contained in a given range of pore size. The pore area within the pore size range 20 to 50 Angstoms can be readily derived.

vi) Leaching

In this work the biocide carrier particles were added to water in the ratio of 0.3:1 biocide carrier to water. An amount of this blend was chosen to ensure that when it was added to 1000 ml of water the solubility maximum for OIT of 400 ppm would not be exceeded. CIT and MIT are both more water soluble than OIT.

The method employed was as follows: 0.75 g of biocide was added to 2.5 g of carrier material. This was then transferred to a vessel and homogenised by rotating the vessel on rollers for 8 hours. The homogenised blend was then charged into 1000 ml of distilled water, stirring continuously. Aliquots of the slurry were taken at intervals of 0.5, 1, 2, 4, 6, 12, 30, 60 and 90 minutes and it was established that after 60 minutes the elution curve plateaued and to ensure that equilibrium had been secured. The experimental work was conducted using a 90 minute equilibrium time. These were filtered and diluted to a concentration within the range of the calibration curve for the respective biocide under investigation. The samples were then analysed by $2^{nd}$ derivative UV/VIS spectroscopy as described above.

vii) Fungicidal Assessment Of Coatings

This method was developed so that fungicidal activity of a biocide within a coating could be evaluated. It can be used to investigate the effects of, for example, water leaching, film weight and concentration on the diffusivity of the biocide.

Coatings with and without the biocide were brush applied in two separate coatings (24 hours between each coating) to one side of rubber discs (3.7 cm in diameter). Once dry, the discs were immersed in 30 ml of sterile distilled water for 1 hour and then dried in a laminar flow cabinet overnight. Potato dextrose agar plates in Petri dishes were prepared, dried and separately inoculated with 1 ml of spore suspensions containing c.a. $10^6$ cfu/ml of each test fungus. Four fungal species were included in the study: *Aureobasidium pullulans* (FS103), *Rhodotural robra* (FS83), *Cladosporium cladosporioides* (IMI71749R) and *Alternaria alternata* (IMI78517). The suspensions were allowed to adsorb into the agar to remove surface wetness. The coated discs were then placed, with coated face down, at the centre of the agar carrying Petri dish. The assembly of plate/disc was then stored in refrigerator for 24 hours to allow diffusion of the biocide to occur. The plates were subsequently placed in an incubator at 25° C. for 5 days. Zones of inhibition were calculated by summing the radial distances as measured from the edge of the filter paper to the fungal growth front at diametrically opposite locations of the disc.

viii) Minimum Inhibition Concentration

The minimum inhibition concentration (MIC) is a measure of the potency of a biocide and comprises the minimum concentration (ppm) of a biocide active or formulation (normally quoted in terms of the active ingredient) determined experimentally in vitro to prevent the growth of a pure culture of a reference microorganism. Although the experimental design may differ, as there are no standard methods, the general principles of the necessary procedures remain the same.

A standardised culture of the microbe under lest is prepared. Aliquots are added to a suitable liquid nutrient medium in stoppered glass tubes containing a range of concentrations of the active biocide. The mixtures are incubated at a standard controlled temperature to encourage growth of the microbes for a standard time, usually between 24 to 48 hours. The tubes are removed and assesed for growth/no growth by measuring the increase in the optical density of the medium caused by an increase in the number of microoganisms present. Other detection methods such as total viable counts or visual examination may be used. The concentration at which no growth is detected is the minimum inhibition concentration (MIC) for that particlar biocide and reference organism. The measurements can be refined by repeating the test using intermediate concentrations of the biocide, between those already chosen as being representative of the killing range, in order to more accurately define the MIC.

ix) Water Leaching of Paint Discs

The method allows an assessment of the level of protection afforded by incorporating a biocide into a paint formulation. Filter discs (Whatman International Limited, Maidstone, Kent), Type 54, hardened 42.5 mm diameter were brush painted on one side of the disc with the test paints (24 hours between coats, 3 replicates per paint) to give an average loading of 0.05 g dried paint. The painted discs were cured at 60° C. for 2 days. One set of discs is then washed with a large volume of distilled water (20 liters) under controlled flow for 24 hours at ambient temperatures.

A freeze dried ampoule of *Cladosporium cladosporioides* (strain no. FS33 ex. Paint Research Association, Teddington, UK) was revived on potato dextrose agar (Oxoid Limited, Basingstoke, UK). A spore innoculum was prepared from the resultant sporing culture (5–7 days growth at 25° C.) by adding 5 ml of sterile distilled water to the surface of the culture on the agar and gently rubbing the surface with a sterile loop to dislodge the spores' mycelium. The resultant suspension was filtered through sterile wool and the filtrate used to seed molten (45° C.) potato dextrose agar prior to pouring into sterile Petri dishes.

Each painted disc was placed on the surface of the seeded agar plate, and the plates placed in a fridge (6–8° C.) for 24 hours to allow diffusion of the biocide. After this period, they were transferred to an incubator at 25° C. for five days. The diameter of the disc, plus any zone of inhibition (no fungal growth) around the discs was measured. An average of the three replicates is taken as a data point.

ix) Prolonged Protection on Paint Panels

Candidate carrier materials dispersed in water borne acrylic emulsion paint were subjected to the procedure of BS 3900: Part G6: 1989 to assess their long term fungicidal efficiency when compared with the biocide added directly to the paint.

Masterboard panels (150 mm×150 mm) were brush coated on one side with the test paints (2 coats, 24 hours between coats) and cured at 60° C. for two days. The coated panels were then weathered in a QUV apparatus (The Q-Panel Co. Bolton, UK) under the following conditions: 125±5 hours exposure to UVA (340 nm) at 40° C. with 1 hour water spray at approximately 24 hour intervals (5 in total). During the water spray the temperature cools to about 20° C.

After weathering the panels were cut into two equal samples and subjected to the procedure described in BS 3900: Part G6:1989. The control paint was the test paint without biocide. *Alternaria altarnata* was included in the standard mixed inoculum of BS 3900: Part G6: 1989.

Visual examination of the panels was carried out after 28, 36 and 84 days. In accordance with the standard procedure, the percentage cover of each panel by fungal growth was assessed.

x) Gas Chromatography Mass Spectrometry (GCMS)

Stock solutions, and particularly those containing blends of isothiozoline based biocides, are analysed using the technique known as GCMS. Quantitative GCMS is carried out using a Hewlett Packard 5890 A gas Chromatograph connected to a VGMS 70-70F Mass spectrometer. The VGMS 70-70F is a double focusing mass spectrometer. The 70° 20 cm radium eletrostatic sector is followed by a 70° 12.7 cm radius magnetic sector. The electron multiplier is a 17 stage venetian blind type with beryllium-copper dynodes, which typically would be operated with a gain of $10^6$.

The GC column was carbowax 20 m, a polyethylene glycol of MW 20.000. Column dimensions were 25 meters length×0.25 mm internal diameter and the carrier gas was Helium (1.0 ml/minute). Solutions for analysis were made up in dichloromethane; where necessary solvent extraction was also carried out with dichloromethane. All sample preparation was carried out in Grade A glassware. Eppendorf auto pipettes were used for sampling; weighing was carried out to 4 figures. DCOIT was used as an internal standard and a separate calibration curve was constructed using a least-squares linear regression algorithm to determine the concentration of biocide present in the sample. The internal sample for OIT analysis was prepared from 0.1 g of DCOIT (99%) dissolved in 20 ml total volume with methanol (concentration 5000 ppm). The internal standard for CIT/MIT analysis was made up from 0.15 g of DCOIT(99%) dissolved in 50 ml total volume with dichloromethane (concentration(3000 ppm). Each sample containing OIT was evaporated down and dosed with 0.25 ml of the internal standard then adjusted to a volume of 5 ml with methanol. The CIT/MIT samples were extracted from aqueous solution with 2×8 ml aliquots of dichloromethane, dosed with 1.6 ml of the internal standard and then adjusted to 20 ml with dichloromethane. The mass spectrometer was calibrated with heptacosafluorotributylamine at a mass range of 45–450 daltons. One scan was obtained per 1.5 $secs^{-1}$. The retention time for each biocide was determined, together with the relative mass for the separated components.

SPECIFIC DESCRIPTION OF THE INVENTION

The following examples serve to illustrate but not limit the present invention. In all the examples, unless otherwise stated the following biocides have been used. The definition of isothiazolone biocide as used here corresponds to the general structural formula shown below.

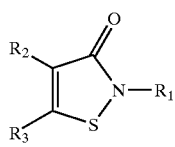

4-$R_2$-5-$R_3$-2-$R_1$-4-Isothiazolin-3-one $R_1$ is an alkyl group with the formula —$(CH_2)_n CH_3$ where n=1 to 8
$R_2$ can be either H or Halogen, and
$R_3$ can be either H or Halogen
Some examples of this class of compounds are included below
DCOIT

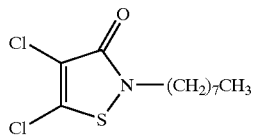

4,5-Dichloro-2-Octyl-4-Isothiazolin-3-one (DCOIT)
ACTICIDE®45-OIT

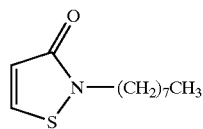

2-Octyl-4-Isothiazolin-3-one (OIT)

46.9% OIT in Propylene Glycol
ACTICIDE®14L-CIT/MIT

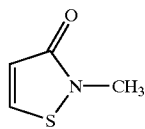 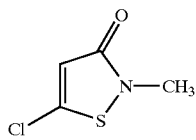

| 2-Methyl-4-Isothiazolin-3-one (MIT) | 5-Chloro-2-Methyl-4-Isothiazolin-3-one (CIT) |

10.3% CIT/3.8% MIT (14.1% Active), in Water
ACTICIDE®TL666-CIT/MIT

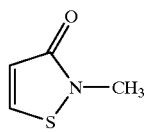 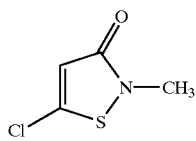

| 2-Methyl-4-Isothiazolin-3-one (MIT) | 5-Chloro-2-Methyl-4-Isothiazolin-3-one (CIT) |

2.5% or less Active in glycol as a ratio of CIT/MIT

Example 1

To allow screening tests to be conducted on a small laboratory scale the biocide impregnated inorganic particulate carriers hereinafter described were made according to the following procedure. The appropriate amount of biocide was added dropwise, 0.7 g of biocide to 2.5 g of carrier material, and then homogenised by rotating the vessel containing the blend on rollers for 8 hours. The impregnated inorganic particulate carrier particles were then charged into 1000 ml of distilled water and allowed to equilibrate for 90 minutes under stirring. The suspension was filtered and the level of biocide analysed in the filtrate using 2nd derivative UV/VIS spectroscopy as previously described. By simple difference the % retained by the carrier could be calculated. The results obtained for the carrier materials impregnated with OIT are given in Table I.

TABLE I

| Sample No. | Material | Si:Al Ratio | B.E.T. Surface Area $m^2/g$ | Average Particle Size microns | OIT Retention % By Weight |
|---|---|---|---|---|---|
| SD1866 | Amorphous Silica | | 728 | 4.6 | 14 |
| SD1866(c) | Amorphous Silica | | 562 | 4.3 | 74 |
| SD1913 | Amorphous Silica | | 395 | 6.2 | 5 |
| SD1913(c) | Amorphous Silica | | 368 | 6.5 | 42 |
| SD1868 | H-Y Zeolite | 5.3:1 | 581 | 4.4 | 27 |
| SD2209 | Y-Zeolite dealumntd. | 33:1 | 733 | 5.5 | 99 |
| SD1867 | 4A-Zeolite | 2.0:1 | 20 | 1.5 | 0 |
| SD2006 | H-Y Zeolite | 5.2:1 | 600 | 3.5 | 33 |
| SD2210 | Hydrotalcite | | 178 | 9.3 | 10 |
| Celite 545 | Diatomaceous Earth | | <10 | 57 | 0 |

The materials labelled SD are inorganic materials available from Crosfield Ltd., Warrington, England. The suffix (c) denotes the material has been heat treated for 2 hours at 700° C. Celite 545, which is referred to in U.S. Pat. No. 4,552,591, is a commercially available product available from World Minerals, Celite UK Limited of Livingstone Road, Hessle, Hull, North Humberside, HU13 OEG. It can be seen that Celite 545 has no affinity for the biocide and is equally as ineffective at retaining the biocide as 4A zeolite and hydrotalcite and many others which are not reported in Table 1. In contrast, the H—Y zeolite, the dealuminated form of Y-zeolite and the heat treated amorphous silicas SD1866(c), SD1913(c) all have a significant propensity to adsorb and retain OIT.

Example 2

Those carrier particles which, from Example 1, were found to exhibit the highest retention of OIT were also investigated for their capability to adsorb CIT/MIT, a higher potency biocide than OIT, and were compared with Celite 545 and 4A-zeolite. To obtain information on the micropore system present in the materials investigated, nitrogen adsorption isotherms were determined to allow calculation of the pore area within the micropore size range of 20 to 50 angstroms. In Table II, the micropore area is listed together with the retention values for OIT and CIT/MIT. In addition, to distinguish between the retention values of the biocides and their potencies, a Retention Factor R has been calculated for the materials investigated. The Retention Factor R is the quotient A/P of the % of active ingredient A by weight remaining in the pore system after contacting with water under the conditions prescribed and the potency P of the biocide as measured on the basis of the reference microorganism, *Aureobasidium pollulens*, in terms of the Minimum Inhibition Concentration (MIC), which for OIT and CIT/MIT is 36 and 5 mg/l respectively.

TABLE II

| Sample No. | Pore Area m²/g 20 to 50 Angstroms | OIT Retention % by weight | CIT/MIT Retention % by weight | Retention Factor R OIT | Retention Factor R CIT/MIT |
|---|---|---|---|---|---|
| SD1866(c) | 211 | 74 | 15 | 2.05 | 3 |
| SD1913(c) | 46 | 42 | 15 | 1.2 | 3 |
| SD1868 | 38 | 27 | 0 | 0.75 | 0 |
| SD1867 (4A-zeolite) | 0 | 0 | 0 | 0 | 0 |
| SD2209 | 64 | 99 | 15 | 2.75 | 3 |
| SD2006 | 48 | 33 | 0 | 0.92 | 0 |
| Celite 545 | 0 | 0 | 0 | 0 | 0 |

It can be seen from Table II that those materials identified for their good retention of biocide in Example 1 have a Retention Factor R in excess of 0.6 for the two biocides, compared with the prior art materials Celite 545 and 4A-zeolite for which the value is zero. The retentive materials were found to have pore areas in the pore size range 20 to 50 Angstrom of greater than 35 m²/g indicating their potential for controlled release of biocide into a substrate, such as a paint or lacquer system.

Example 3

To produce larger samples of the biocide impregnated inorganic carriers for testing in paint formulations the following method was utilised. The appropriate amount of biocide was added dropwise to the inorganic particulate carrier (500 g) whilst it was being stirred in a Sirman SV6 Food Processor (available from Metcalf catering Equipment, Bleanau Ffestinlog, Gwyndd, Wales) so that the finished product contained 27% by weight of the biocide. The biocide impregnated particulate carrier composition was then sealed in a tin to prevent the loss of volatile components and to allow the blend to equilibrate before mixing into a paint system. The following method was used to disperse the biocide carrier composition in the paint formulation.

The appropriate amount of the biocide carrier composition needed to yield a dry film concentration of 100 ppm for CIT/MIT and 600 ppm for OIT was added to 1 kg of the paint formulation retained in a suitably sized vessel. The dispersion could then be agitated with a Cowles high speed disperser. This premix was then transferred to a Silverson type mixer, fitted with a medium mixing head, and mixed until a finer dispersion was obtained. Control formulations containing only (I) the free biocide and (ii) free biocide plus unloaded inorganic carrier particles were prepared in exactly the same way so as to eliminate the method of dispersion as a variable. For each preparation, during dispersion on the Silverson Mixer, the temperature of the vessel was controlled between 40 to 50° C. The two model paint formulations, one a water-borne acrylic and the other a solvent-based alkyd used in this example had the following compositions:

| Solvent-based alkyd | % By Weight |
|---|---|
| White Spirit | 19.5 |
| Urethane Alkyd (55% in white spirit) | 78.2 |
| Cobalt Drier | 0.4 |
| Zirconium Drier | 0.4 |
| Calcium Drier | 0.8 |
| Methyl Ethyl Ketoxime | 0.1 |
| Defoamer | 0.6 |

(Urethane Alkyd as supplied under the trade name Unithane 655W by Cray Valley of Waterloo, Machen, Newport, Gwent NP1 8YN, UK)

Water-Borne Acrylic

Acrylic Emulsion

Dispelair CF269 Added as Required to Counteract Foaming (Acrylic emulsion as supplied, devoid of protective biocidal additive, under the trade name Revacryl 1A by Harlow Chemical Co. and Dispelair CF269 defoamer supplied by Blackburn Chemicals)

The biocidal efficacy in the above paint formulations of the range of carriers loaded with OIT or CIT/MIT were compared with the biocides in non-loaded systems. A rapid screening test using *Cladosporium cladosporioides* was used to determine the zones of inhibition around cured, painted rubber discs placed, coated face down, on a solid agar surface seeded with the fungus as described hereinbefore. Tables III and IV summarise the data obtained on the water-borne acrylic and the alkyd paint systems containing free OIT, added only as the biocide to the paint formulation (Free), OIT loaded onto the carrier (SDno.(L)) and free OIT together with the unloaded inorganic carrier (Free+SDno.). SDno denotes the SD number of the inorganic carrier as listed in Tables III and IV. To highlight distinguishing features in performance, the concentration of OIT in the paint film ranged from 600 to 12000 ppm for both the acrylic and the alkyd paint system, irrespective of the method of addition of the biocide to the formulation.

TABLE III

Acrylic Paint Formulation

| Paint Formuln. | OIT Concn. ppm | Addition Method | Zone Present | Zone Size mm |
|---|---|---|---|---|
| P1 | 600 | Free | + | <1 |
| P2 | 1,000 | Free | + | <1 |
| P3 | 2,000 | Free | + | 7 |
| P4 | 4,000 | Free | + | 10 |
| P5 | 8,000 | Free | + | 18 |
| P6 | 12,000 | Free | + | 20 |
| P7 | 600 | SD2209(L) | + | <1 |
| P8 | 1,000 | SD2209(L) | + | <1 |
| P9 | 2,000 | SD2209(L) | + | 3 |
| P10 | 4,000 | SD2209(L) | + | 9 |
| P11 | 8,000 | SD2209(L) | + | 13 |
| P12 | 12,000 | SD2209(L) | + | 18 |
| P13 | 600 | Free + SD2209 | + | <1 |
| P14 | 1,200 | Free + SD2209 | + | <1 |

TABLE IV

Alkyd Paint Formulation

| Paint Formulation | OIT Concn. ppm | Addition Method | Zone Present | Zone Size mm |
|---|---|---|---|---|
| P15 | 1,200 | Free | + | <1 |
| P16 | 2,000 | Free | + | 2 |
| P17 | 4,000 | Free | + | 3 |
| P18 | 8,000 | Free | + | 5 |
| P19 | 12,000 | Free | + | 10 |
| P20 | 1,200 | SD2209(L) | + | <1 |
| P21 | 2,000 | SD2209(L) | + | 1 |
| P22 | 4,000 | SD2209(L) | + | 3 |
| P23 | 8,000 | SD2209(L) | + | 4 |
| P24 | 12,000 | SD2209(L) | + | 5 |

The "zone sizes" referred to above are the summed radial distances, as previously mentioned.

In Tables III and IV, "+" indicates that there was an observable zone of fungal inactivity around the periphery of the painted disc. It can be seen that under the test conditions the response for OIT is not significant in the concentration range 600 to 1,000 ppm in either paint formulation. To measure the levels of inhibition imparted by the biocide, the concentrations in the paint film need to be increased to values in excess of 1,200 ppm and, in the range 1,200 to 12,000 ppm. It is then possible to see differences produced by the different modes of introducing the biocide into the paint formulation. In both formulations there is clear evidence that incorporation of biocide to the paint system in the form as adsorbed in the pore system of the inorganic particulate carrier is slowing down the response for OIT. This can be seen by comparing the size of the zones of inhibition for the paint formulations containing high concentrations of biocide. For the alkyd system at a loading of 12,000 ppm of OIT there is marked reduction in the zone width, from 10 to 5 mm, between the paint formulation containing free biocide and the one where the biocide has been added adsorbed in the pore system of the inorganic particulate carrier. For the water borne acrylic the difference in zone widths is not as marked (20 mm compared with 18 mm for paint formulations containing 1,2000 ppm of OIT). However, in general on comparing the inhibition zones obtained for the range for the formulations containing 2000 to 8000 ppm there is sufficient evidence to support the observation that, in this paint system, the response is being slowed by incorporating the biocide on the inorganic particulate carrier.

Example 4

The data in Example 3 was measured on model paint systems. In order to investigate the effect of the biocide carrying particles in a so-called real paint system the following formulation, representing water based high build paint-type, was chosen.

| Water based High Build | % By Weight |
|---|---|
| Styrene Acrylic Emulsion (50%) | 43.7 |
| Sodium Hexametaphosphate (33%) | 1.01 |
| Potassium Oleate (18.6%) | 2.8 |
| Aluminium Silicate | 2.5 |
| Anionic Surfactant (35%) | 2.6 |
| Titanium Dioxide Dispersion (68%) | 20.2 |
| Water | 1.8 |
| Cellulose Thickener | 0.3 |
| Barytes | 20.5 |
| Butyl Diglycol Acetate | 0.90 |
| White Spirit | 1.20 |
| Glass Microspheres | 2.16 |
| Defoamer | 0.33 |
| Weight % Solids | 63.52 |
| Volume % Solids | 46.77 |
| Pigment Volume Concentration (%) | 40.83 |
| Specific Gravity | 1.45 |

Using this formulation as the base, biocides (OIT and DCOIT) were added either as the free biocide or as the biocide carrying particles to produce a range of paints of varying biocide content from zero (control) to 4,000 ppm.

The biocidal efficiency of the two carriers (SD 2209 and SD 1866) loaded, at 30% by weight, with OIT and DCOIT in the acrylic high build formulation was compared before, and after, a 24 hours leach using procedure (ix) described hereinbefore. The paints containing the biocide carrying particles and those where the biocide was incorporated as the free biocide where used in the example.

TABLE V

The effect of biocide loaded carriers in an acrylic paint on the inhibition of *Cladesporium cladosporioides*

| Sample | Biocide Concentration ppm | Zone of Inhibition Before Leaching | Zone of Inhibition After Leaching |
|---|---|---|---|
| SD 2209/OIT | 300 | 30 | 7 |
|  | 1,200 | >42 | 9 |
|  | 4,000 | >42 | >42 |
| SD 1866/OIT | 300 | 33 | 5 |
|  | 1,200 | 36 | 11 |
|  | 4,000 | >42 | 38 |
| SD 2209/DCOIT | 300 | 9 | 7 |
|  | 1,200 | 14 | 6 |
|  | 4,000 | 30 | 16 |
| SD 1866/DCOIT | 300 | 21 | 5 |
|  | 1,200 | 24 | 8 |
|  | 4,000 | 27 | 14 |
| Free OIT | 300 | 32 | Overgrowth |
|  | 1,200 | >42 | 1 |
|  | 4,000 | >42 | 1 |
| Free DCOIT | 300 | 22 | Overgrowth |
|  | 1,200 | 25 | 1 |
|  | 4,000 | 38 | 2 |
| Blank Control | — | 7 | Overgrowth |

Inhibition zone size = Total diameter of zone – Disc Diameter 425 mm
Fiqures listed above in Table V are an average of 3 replicates.

Clearly, the paint films containing the loaded carriers retained more biocidal activity after leaching than those containing the free biocides.

To further distinguish performance the inoculated petri dishes containing the painted discs were incubated for a further 14 days so as to examine the extent of encroachment of the fungi into the surface of the paint film. The dishes were removed from the incubator and the surface of the paint discs examined for growth.

TABLE VI

The effect of biocide loaded carriers in acrylic paint on the surface inhibition of *Cladosporium cladosporioides*

| Sample | Biocide Concentration ppm | Zone of Inhibition Before Leaching | Zone of Inhibition After Leaching |
|---|---|---|---|
| Free OIT | 300 | None | Growth |
| SD 2209/OIT | 300 | None | None |
| SD 1866/OIT | 300 | None | None |
| Free DCOIT | 300 | None | Growth |
| SD 2209/DCOIT | 300 | None | None |
| SD 1866/OIT | 300 | None | None |

The data shows that the paint formulations containing the biocide loaded on the carriers are capable of providing protection to the surface of the paint films, even after water leaching, against the ingress of the test fungi. The paints formulated with free biocides exhibited no resistance to the fungi after the prepared paint films were leached with water.

Example 5

Following on from the observations of Example 4, the two carriers SD 2209 and SD 1866 loaded, at 30% by weight, with OIT and DCOIT were incorporated into the paint formulation specified in Example 4 and subjected to BS 3900: Part G6 as described in procedure (x) hereinbefore to assess their long term film fungicidal efficiency in comparison with OIT and DCOIT added directly to the paint.

Masterboard panels (150 mm×150 mm) were brush coated on one side with the test paints (2 coats, 24 hours between coats) and cured at 60° C. for two days. The coated panels were then weathered in a QUV apparatus as described hereinbefore in procedure (x). After weathering the panels were cut into two equal samples and subjected to the procedure described in BS 3900: Part G6: 1989. The panels were exposed for 28, 36, and 84 days, in accordance with the standard procedure, and the percentage cover of each panel by fungal growth was assessed at these stages.

TABLE VII

Fungal growth ratings (% cover) for weathered painted Masterboard Panels against time (days)

| Sample | Biocide Concentration ppm | % Cover D28 | % Cover D56 | % Cover D84 |
|---|---|---|---|---|
| SD 2209/OIT | 300 | 15 | 25 | 33 |
|  | 1,200 | 0 | 12 | 22 |
|  | 4,000 | 0 | 0 | 0 |
| SD 1866/OIT | 300 | 35 | 32 | 45 |
|  | 1,200 | 5 | 3 | 5 |
|  | 4,000 | 0 | 0 | 0 |
| Free OIT | 300 | 35 | 85 | 85 |
|  | 1,200 | 3 | 35 | 35 |
|  | 1,400 | 0 | 0 | 5 |
| SD 2209/DCOIT | 300 | 10 | 68 | 78 |
|  | 1,200 | 0 | 35 | 35 |
|  | 4,000 | 0 | 0 | 0 |
| SD 1866/DCOIT | 300 | 35 | 77 | 83 |
|  | 1,200 | 8 | 25 | 27 |
|  | 4,000 | 0 | 0 | 0 |
| Free DCOIT | 300 | 23 | 85 | 85 |
|  | 1,200 | 8 | 55 | 68 |
|  | 4,000 | 0 | 0 | 5 |
| Control | — | 45 | 85 | 100 |

1. Results are averaged from ratings for two panels and corrected to nearest whole number.
2. D28, D56 and D84 relate to Day 28, Day 58 and Day 84.

The data presented in Table VII shows that there are significant differences in the amount of fungal growth observed on the paints formulated with, and without, the biocide carrying particles. This is particularly evident at the 1,200 ppm level of biocide addition confirming the observations of Example 4 that this indeed is a threshold at which leaching effects are greatest between the loaded and free biocide. It can also be seen that weathering (a combination of UV exposure and water leaching) has a greater effect on the paints containing the free biocide carrying particles. The data confirms that there is greater control of leaching of the loaded biocide from the paint film, than the free biocide. As the test is an environmental simulation, there is strong evidence that the paint containing the loaded biocide carrier will have better performance in service than the one formulated with free biocide present.

Example 6

It is well known that isothiozolin-based biocides are susceptible to degradation on storage at intermediate temperature (60° C.) and when exposed to U.V. irradiation. The purpose of this example is to demonstrate the benefit of pre-adsorbing the biocide into the pore structure of the inorganic carrier.

The biocides used in this example were prepared as stock solutions as listed below:

TL666 1.55% total active in 2.7:1 ratio C1T:M1T

OIT 50.98% in cyclohexane

The solutions of biocides were added dropwise to slowly stirring powder beds of SD 1866 and SD 2209, respectively, until a loading of 0.3 g. of biocide solution per g. of carrier was obtained as described hereinbefore.

The loaded biocides, together with the stock solutions, were spread on petri dishes and either placed in an incubator at 60° C. or exposed to U.V. irradiation in a Microscal unit (Miscoscal Limited, London) fitted with a 500 W high pressure mercury/tungsten lamp (wavelength>300 nm) operating at temperature 50° C. and a relative humidity in the region of 50%. These conditions of exposure are referred to hereinafter as the defined conditions of UV exposure and thermal ageing. Samples were withdrawn from the petri dishes undergoing thermal treatment and exposure to U.V. irradiation on a regular basis over a period in the region of 50 days. The amount of biocide remaining in each withdrawn sample was determined at the time of withdrawal using second derivative U.V.-visible Spectroscopy. The amount of biocide remaining in the stock solutions was determined by Gas Chromatography Mass Spectrometry. Relative peak heights corresponding to the residual parts of OIT, CIT and MIT were used to determine the concentrations of biocide in each sample. In the case of TL666 the ratio of the relevant peak heights were used to arrive at the concentrations of CIT and MIT in the aged stock solution.

TABLE VIII

Thermal Ageing

| Days | OIT Stock Solution | SD 1866 + OIT | SD 2209 + OIT |
|---|---|---|---|
| 0 | 100 | 100 | 100 |
| 3 |  | 96 | 68 |

TABLE VIII-continued

Thermal Ageing

| Days | OIT Stock Solution | SD 1866 + OIT | SD 2209 + OIT |
|---|---|---|---|
| 6 |  | 94 | 63 |
| 7 | 80 |  |  |
| 12 | 78 |  |  |
| 18 | 65 |  |  |
| 19 |  | 84 | 65 |
| 26 |  | 88 | 62 |
| 33 |  | 74 | 60 |
| 40 | 50 | 83 | 59 |
| 42 |  | 68 | 55 |
| 47 |  | 55 | 50 |

TABLE IX

Thermal Ageing

| Days | MIT Stock solution | CIT Stock solution | SD 1866 + MIT/CIT | SD 2209 + MIT/CIT |
|---|---|---|---|---|
| 0 | 100 | 100 | 100 | 100 |
| 3 |  |  | 93 | 85 |
| 6 |  |  | 89 | 85 |
| 7 | 95 | 80 |  |  |
| 12 | 90 | 40 | 75 | 89 |
| 18 | 80 | 30 |  | 85 |
| 19 |  |  | 75 | 84 |
| 26 |  | 0 | 63 | 81 |
| 33 |  |  | 59 | 81 |
| 40 | 50 |  | 57 | 79 |
| 47 |  |  | 52 | 79 |

From the stock solutions of CIT and MIT and the proportions of CIT and MIT, it can be calculated that the equivilant amount of biocide that would remain in a stock solution containing MIT/CIT would be in the region of 14% w/w after a thermal ageing period in the region of 40 days.

TABLE X

U.V. Irradiation

| Days | MIT Stock solution | CIT Stock solution | SD 1866 + MIT/CIT | SD 2209 + MIT/CIT |
|---|---|---|---|---|
| 0 | 100 | 100 | 100 | 100 |
| 7 | 78 | 0 | 80 | 93 |
| 13 |  |  | 66 | 90 |
| 20 |  |  | 65 | 72 |
| 25 | 69 | 0 |  |  |
| 32 | 62 | 0 |  |  |
| 34 |  |  | 46 | 69 |
| 39 | 50 | 0 |  |  |
| 41 |  |  | 43 | 67 |
| 55 | 24 |  | 40 | 72 |

From the stock solutions of CIT and MIT and the proportions of CIT and MIT therein, it can be calculated that the equivalent amount of biocide that would remain in a stock solution containing MIT/CIT would be in the region of 14% w/w after exposure to UV irradiation for an ageing period in the region of 40 days.

TABLE XI

U.V. Irradiation

| Days | OIT Stock solution | SD 1866 + OIT | SD 2209 + OIT |
|---|---|---|---|
| 0 |  | 100 | 100 | 100 |
| 7 | 62 | 93 | 52 |
| 13 |  |  | 37 |
| 14 | 17 |  |  |
| 20 |  | 90 | 35 |
| 34 |  | 95 | 42 |
| 41 |  | 97 | 45 |
| 42 | 1 | 93 | 48 |
| 55 |  | 92 | 45 |

The data in Tables XIII and IX indicate that the biocide adsorbed in the pore system has been offered some protection from thermal degradation. There is also evidence that there is a significant difference in the performance of the silica (SD 1866) versus the zeolite (SD 2209) with the biocide degrading slightly faster when associated with the zeolite.

The data in Tables X and XI compare the rates of U.V. degradation as the amounts of original biocide remaining over 55 days for CIT/MIT and OIT respectively. Clearly, the biocide adsorbed in the pore system of the carrier is more stable to UV irradiation than the biocide in the stock solution.

As expected, exposure to UV irradiation is more severe than thermal treatment, in that both the free and adsorbed biocide degrades more rapidly over the same time period. The exception to this observation is OIT on silica (SD 1866) where there is no significant degradation of the biocide over the 55 days exposure. There is also evidence that the silica carrier (SD 1866) offers more protection to the biocide than zeolite framework (SD 2209).

What is claimed is:

1. A particulate composition of matter comprising a liquid dispersible mass of porous inorganic carrier particles which is at least one of amorphous silicas, amorphous aluminas, pseudoboehmites, Y-zeolites, dealuminated Y-zeolites or mixtures of two or more thereof and biocide releasably adsorbed within the pore system thereof, said particles having a retention factor R, determined from the equation R=A/P, where A represents the percentage active ingredient by weight remaining in the pore system after contacting a sample consisting of a homogenised mixture of 0.75 g biocide and 2.25 g of carrier particles with 1000 ml of water for 90 minutes and P represents the potency as defined by the Minimum Inhibition Concentration in mg of active ingredient per liter of the biocide determined with respect to the reference microorganism Aureobasidium pullulans, of at least 0.6, and a BET surface area of at least 200 m$^2$ g, wherein the biocide is at least one of 2-methyl-4-isothiazolone, 2-ethyl-4-isothiazolin-3-one, 2-propyl-4-isothiazolin-3-one, 2-butyl-4-isothiazolin-3-one, 2-amyl-4-isothiazolin-3-one, 5-chloro-2-methyl-4-isothiazolin-3-one, 5-bromo-2-methyl-4-isothiazolin-3-one, 5-iodo-2-methyl-4-isothiazolin-3-one, 5-chloro-2-butyl-4-isothiazolin-3-one, 5-bromo-2-ethyl-4-isothiazolin-3-one, 5-iodo-2-amyl-4-isothiazolin-3-one, 1,2-benzisothiazolin-3-one, 2-n-octyl-4-isothiazolin-3-one, or 4,5-dichloro-2-n-octyl-4-isothiazolin-3-one.

2. A composition as claimed in claim 1 in which the retention factor is at least 0.8.

3. A composition as claimed in claim 1 in which the particles carry at least 30% by weight of biocide solution.

4. A composition as claimed in claim 1 in which the particles have an activated micropore system.

5. A composition as claimed in claim 1 in which the particles have a BET surface area of at least 300 m$^2$/g.

6. A composition as claimed in claim 1 in which the particles have a biocide adsorption capacity of at least 10% by weight.

7. A liquid-based medium incorporating the particulate composition as claimed in claim 1, said liquid medium comprising a surface coating composition, a surface cleaning composition, a sealant composition, a tiling composition, a grouting composition or a drilling mud.

8. A liquid-based medium incorporating the particulate composition as claimed in claim 3, said liquid medium comprising a surface coating composition, a surface cleaning composition, a sealant composition, a tiling composition, a grouting composition and a drilling mud.

9. A surface coating formulation as claimed in claim 1 in the form of a water-based or organic solvent-based paint.

10. A composition as claimed in claim 1 in which the particles have:

a weight mean particle size less than 50 microns.

11. The composition of claim 1 wherein said particles have a pore area of at least 25 m$^2$/g.

12. A particulate composition of matter comprising a liquid dispersible mass of porous inorganic carrier particles which are Y-zeolites with, optionally, amorphous silicas, dealuminated Y-zeolites, or mixtures of two or more of these and biocide releasably adsorbed within the pore system thereof, said particles having a retention factor R, determined from the equation R=A/P, where A represents the percentage active ingredient by weight remaining in the pore system after contacting a sample consisting of a homogenised mixture of 0.75 g biocide and 2.25 g of carrier particles with 1000 ml of water for 90 minutes and P represents the potency as defined by the Minimum Inhibition Concentration in mg of active ingredient per liter of the biocide determined with respect to the reference microorganism *Aureobasidium pullulans*, of at least 0.6, and a BET surface area of at least 200 m$^2$/g, wherein the biocide is at least one of 2-methyl-4-isothiazolone, 2-ethyl-4-isothiazolin-3-one, 2-propyl-4-isothiazolin-3-one, 2-butyl-4-isothiazolin-3-one, 2-amyl-4-isothiazolin-3-one, 5-chloro-2-methyl-4-isothiazolin-3-one, 5-bromo-2-methyl-4-isothiazolin-3-one, 5-iodo-2-methyl-4-isothiazolin-3-one, 5-chloro-2-butyl-4-isothiazolin-3-one, 5-bromo-2-ethyl-4-isothiazolin-3-one, 5-iodo-2-amyl-4-isothiazolin-3-one, 1,2-benzisothiazolin-3-one, 2-n-octyl-4-isothiazolin-3-one, or 4,5-dichloro-2-n-octyl-4-isothiazolin-3-one.

13. A particulate composition of matter comprising a liquid dispersible mass of porous inorganic carrier particles which are dealuminated Y-zeolites with, optionally, amorphous silicas, Y-zeolites, or mixtures of two or more of these and biocide releasably adsorbed within the pore system thereof, said particles having a retention factor R, determined from the equation R=A/P, where A represents the percentage active ingredient by weight remaining in the pore system after contacting a sample consisting of a homogenised mixture of 0.75 g biocide and 2.25 g of carrier particles with 1000 ml of water for 90 minutes and P represents the potency as defined by the Minimum Inhibition Concentration in mg of active ingredient per liter of the biocide determined with respect to the reference microorganism *Aureobasidium pullulans*, of at least 0.6, and a BET surface area of at least 200 m$^2$/g, wherein the biocide is at least one of 2-methyl-4-isothiazolone, 2-ethyl-4-isothiazolin-3-one, 2-propyl-4-isothiazolin-3-one, 2-butyl-4-isothiazolin-3-one, 2-amyl-4-isothiazolin-3-one, 5-chloro-2-methyl-4-isothiazolin-3-one, 5-bromo-2-methyl-4-isothiazolin-3-one, 5-iodo-2-methyl-4-isothiazolin-3-one, 5-chloro-2-butyl-4-isothiazolin-3-one, 5-bromo-2-ethyl-4-isothiazolin-3-one, 5-iodo-2-amyl-4-isothiazolin-3-one, 1,2-benzisothiazolin-3-one, 2-n-octyl-4-isothiazolin-3-one, or 4,5-dichloro-2-n-octyl-4-isothiazolin-3-one.

14. A particulate composition of matter useful as a vehicle for introducing biocide into a liquid-based medium comprising a liquid-dispersible mass of inorganic carrier particles comprising Y zeolite particles having biocide adsorbed within the pore system thereof for release of biocide into the liquid medium, said amorphous Y zeolite particles having a retention factor R, determined from the equation R=A/P, where A represents the percentage active ingredient by weight remaining in the pore system after contacting a sample consisting of a homogenised mixture of 0.75 g biocide and 2.25 g of carrier particles with 1000 ml of water for 90 minutes and P represents the potency as defined by the Minimum Inhibition Concentration in mg of active ingredient per liter of the biocide determined with respect to the reference microorganism *Aureobasidium pullulans*, of at least 0.6, and wherein the biocide is at least one of 2-methyl-4-isothiazolone, 2-ethyl-4-isothiazolin-3-one, 2-propyl-4-isothiazolin-3-one, 2-butyl-4-isothiazolin-3-one, 2-amyl-4-isothiazolin-3-one, 5-chloro-2-methyl-4-isothiazolin-3-one, 5-bromo-2-methyl-4-isothiazolin-3-one, 5-iodo-2-methyl-4-isothiazolin-3-one, 5-chloro-2-butyl-4-isothiazolin-3-one, 5-bromo-2-ethyl-4-isothiazolin-3-one, 5-iodo-2-amyl-4-isothiazolin-3-one, 1,2-benzisothiazolin-3-one, 2-n-octyl-4-isothiazolin-3-one, or 4,5-dichloro-2-n-octyl-4-isothiazolin-3-one.

15. A composition as claimed in claim 14 in which the Y zeolite is a dealuminated Y zeolite.

16. A composition as claimed in claim 14 in which the Si:Al ratio of the Y zeolite is at least about 5:1.

17. A composition as claimed in claim 14 in which the Si:Al ratio of the Y zeolite is in the range from about 5:1 to about 33:1.

18. A composition as claimed in claim 14 in which the retention factor is at least 0.8.

19. A composition as claimed in claim 14 in which the particles carry at least 30% by weight of biocide solution.

20. A composition as claimed in claim 14 in which the particles have an activated micropore system.

21. A composition as claimed in claim 14 in which the particles have a biocide adsorption capacity of at least 10% by weight.

22. A liquid-based medium incorporating the particulate composition as claimed in claim 14, said liquid medium comprising a surface coating composition, a surface cleaning composition, a sealant composition, a tiling composition, a grouting composition or a drilling mud.

23. A liquid-based medium incorporating the particulate composition as claimed in claim 19, said liquid medium comprising a surface coating composition, a surface cleaning composition, a sealant composition, a tiling composition, a grouting composition and a drilling mud.

24. A surface coating formulation as claimed in claim 14 in the form of a water-based or organic solvent-based paint.

25. A composition as claimed in claim 14 in which the particles have a weight mean particle size less than 50 microns.

26. The composition of claim 14 wherein said particles have a pore area of at least 25 m$^2$ $\mu$g.

27. A particulate composition of matter useful as a vehicle for introducing biocide into a liquid-based medium comprising a liquid-dispersible mass of inorganic carrier particles having a pore size range including the range from about 20 to about 50 Angstroms; and a pore area of at least 25 $m^2/g$ in the pore size range from about 20 to about 50 Angstroms and comprising Y zeolite particles having biocide adsorbed within the pore system thereof for release of biocide into the liquid medium, said amorphous Y zeolite particles having a retention factor R, determined from the equation R=A/P, where A represents the percentage active ingredient by weight remaining in the pore system after contacting a sample consisting of a homogenised mixture of 0.75 g biocide and 2.25 g of carrier particles with 1000 ml of water for 90 minutes and P represents the potency as defined by the Minimum Inhibition Concentration in mg of active ingredient per liter of the biocide determined with respect to the reference microorganism *Aureobasidium pullulans*, of at least 0.6.

28. A composition as claimed in claim 27 in which the retention factor is at least 0.8.

29. A composition as claimed in claim 27 in which the particles carry at least 30% by weight of biocide solution.

30. A composition as claimed in claim 27 in which the particles have an activated micropore system.

31. A composition as claimed in claim 27 in which the particles have a biocide adsorption capacity of at least 10% by weight.

32. A liquid-based medium incorporating the particulate composition as claimed in claim 27, said liquid medium comprising a surface coating composition, a surface cleaning composition, a sealant composition, a tiling composition, a grouting composition or a drilling mud.

33. A liquid-based medium incorporating the particulate composition as claimed in claim 30, said liquid medium comprising a surface coating composition, a surface cleaning composition, a sealant composition, a tiling composition, a grouting composition and a drilling mud.

34. A surface coating formulation as claimed in claim 27 in the form of a water-based or organic solvent-based paint.

35. A composition as claimed in claim 27 in which the particles have a weight mean particle size less than 50 microns.

36. A composition as claimed in claim 27 in which the Y zeolite is a dealuminated Y zeolite.

37. A composition as claimed in claim 27 in which the Si:Al ratio of the Y zeolite is at least about 5:1.

38. A composition as claimed in claim 27 in which the Si:Al ratio of the Y zeolite is in the range from about 5:1 to about 33:1.

* * * * *